US012605487B2

(12) United States Patent　　(10) Patent No.: US 12,605,487 B2

Chiesa et al.　　(45) Date of Patent: Apr. 21, 2026

(54) METAL SUBSTRATE WITH ANTIBACTERIAL AND OSTEOINTEGRATIVE PROPERTIES FOR IMPLANTOLOGY APPLICATIONS

(71) Applicant: MEDACTA INTERNATIONAL SA, Castel San Pietro (CH)

(72) Inventors: Roberto Chiesa, Como (IT); Lia Rimondini, Bologna (IT); Francesco Siccardi, Morcote (CH); Angelo De Lollis, Como (IT); Matteo Parravicini, Como (IT)

(73) Assignee: Medacta International SA, Castel San Pietro (CH)

( * ) Notice: Subject to any disclaimer, the term of this patent is extended or adjusted under 35 U.S.C. 154(b) by 882 days.

(21) Appl. No.: 17/626,608

(22) PCT Filed: Jul. 16, 2020

(86) PCT No.: PCT/IB2020/056688

§ 371 (c)(1),
(2) Date: Jan. 12, 2022

(87) PCT Pub. No.: WO2021/014291

PCT Pub. Date: Jan. 27, 2021

(65) Prior Publication Data

US 2022/0241460 A1　Aug. 4, 2022

(30) Foreign Application Priority Data

Jul. 19, 2019　(IT) ........................ 102019000012330

(51) Int. Cl.
A61L 27/30 (2006.01)
A61L 27/06 (2006.01)

(52) U.S. Cl.
CPC ............. A61L 27/306 (2013.01); A61L 27/06 (2013.01); *A61L 2400/18* (2013.01); *A61L 2420/02* (2013.01); *A61L 2430/02* (2013.01)

(58) Field of Classification Search
CPC ...... A61L 27/306; A61L 27/32; A61L 31/086; A61L 31/088; A61L 2400/18; A61L 2420/02
See application file for complete search history.

(56) References Cited

U.S. PATENT DOCUMENTS

| | | | |
|---|---|---|---|
| 2007/0191944 A1* | 8/2007 | Contreras | ............... A61L 27/06 427/2.24 |
| 2014/0021055 A1* | 1/2014 | Chiesa | .................... A61L 27/50 205/223 |

FOREIGN PATENT DOCUMENTS

| | | | | |
|---|---|---|---|---|
| WO | WO-2018174475 A1 * | 9/2018 | ............. | A61C 13/00 |
| WO | WO-2020049299 A1 * | 3/2020 | ........... | A61L 27/047 |

OTHER PUBLICATIONS

English machine translation of WO 2018/174475 A1 made Nov. 15, 2024. (Year: 2024).*
International Search Report and Written Opinion issued in PCT/IB2020/056688, mailed Oct. 28, 2020.
Ishizawa, Hitoshi, and Makoto Ogino. "Formation and characterization of anodic titanium oxide films containing Ca and P." Journal of biomedical materials research 29.1 (1995): 65-72.

* cited by examiner

*Primary Examiner* — Michael B. Pallay
(74) *Attorney, Agent, or Firm* — Meunier Carlin & Curfman LLC

(57) ABSTRACT

The present invention relates to a substrate of a metal, preferably titanium or a titanium alloy, having at least one surface coated with an oxide layer of the metal itself, said surface being modified and enriched with Ca, P, Ga, Sr, and, optionally, Ag by anodic spark deposition (ASD). The present invention also relates to a process for producing said substrate by applying the anodic spark deposition (ASD) technique to a substrate, optionally pre-treated, immersed in an electrolytic solution comprising Ca, P, Ga, Sr and, optionally, Ag. Finally, the present invention also relates to a prosthesis and a surgical implant comprising or preferably produced with said substrate, as well as the use thereof for the prevention of bacterial colonisation and promotion of osteointegration in implantology operations, preferably orthopaedic prosthetic implantology.

27 Claims, 6 Drawing Sheets

NT                 SrGa

Time (days)

Time (days)

Time (days)

Time (days)

METAL SUBSTRATE WITH ANTIBACTERIAL AND OSTEOINTEGRATIVE PROPERTIES FOR IMPLANTOLOGY APPLICATIONS

FIELD OF THE INVENTION

The present invention relates to a substrate of a metal, preferably titanium or a titanium alloy having at least one surface coated with an oxide layer of the metal itself, said surface being modified and enriched with Ca, P, Ga, Sr and, optionally, Ag by anodic spark deposition (ASD) and a process for the production thereof. The present invention also relates to a prosthesis and a surgical implant comprising or preferably produced with said substrate, as well as the use thereof for the prevention of bacterial colonisation and promotion of osteointegration in implantology operations, preferably orthopaedic prosthetic implantology.

BACKGROUND OF THE INVENTION

In recent decades there has been a progressive increase in both orthopaedic and dental prosthetic implantology interventions. As regards orthopaedic prosthetic implantology interventions, the most common and widespread ones involve the replacement of joints, such as, for example, hips and knees. This replacement has the aim not only of replacing, for example, the damaged joint which provokes pain and a limitation of movements, but also of re-establishing its morphology and functionality, thereby enabling a reduction of pain and an improvement in the patient's quality of life. In the field of prosthetics, it is thus of fundamental importance to have an availability of materials that are compatible with biological tissues in order to enable an adequate treatment of patients. At the present state of the art, the materials of first choice for the production of prostheses and/or surgical implants in the realm of orthopaedics or dentistry are often represented by substrates of titanium or alloys thereof, since such materials exhibit excellent characteristics as regards both biocompatibility and elastic modulus, mechanical strength and corrosion resistance. In particular, the biocompatibility of titanium is tied to the presence of a thin passivating oxide layer that is created spontaneously on the surface of the material following its exposure to air and enables the material to be inert once implanted inside the human body. Notwithstanding the characteristics that to date have made titanium the most widely used material in the realm of orthopaedics and/or dentistry, the prostheses and implants produced with this material can be prone to failure for various reasons, including lack of osteointegration and bacterial infection. In fact, one of the disadvantages connected to the use of prostheses and/or implants made of titanium or alloys thereof is that it takes a long time for them to be integrated into the biological tissues of the patients in whom they are implanted, which leads to a slowed or ineffective healing of the implant region, thus causing a greater risk of bacterial proliferation and hence failure of the prosthesis and/or of the implant. Clinical practice shows that precisely the bacterial infections that occur in the implanted devices represent one of the most common causes of failure, taking into account that antibiotic and pharmacological treatment proves to be ineffective in many cases. The consequences of the failure of the operation are removal of the device from the body of the host and its replacement, actions leading not only to an increase in health and social costs, but also to an increase in the risk for the patient. In order to address these problems, or at least limit their occurrence, in recent years various types of treatments have been proposed which are aimed at modifying the surface morphology of the material and improve the characteristics listed above, in particular the characteristics connected to antibacterial and osteointegrative properties. These treatments include so-called "anodic spark deposition" (ASD), an electrochemical treatment which enables titanium or an alloy thereof to be superficially modified so as to obtain substrates having homogeneous titanium oxide surfaces characterised by a generally microporous morphology, and into which it is possible to incorporate chemical agents capable of interacting with biological tissues, thereby improving the integration between the prosthesis and/or implant and tissues.

This technique was applied in a pioneering way by Ishizawa et al. ("H. Ishizawa, "Formation and characterization of anodic titanium oxide films containing Ca and P", Journal of Biomedical Materials Research, Vol. 29, 6572 (1995)) in order to superficially modify a titanium substrate with P and Ca ions. Ishizawa et al. developed an electrolytic solution containing $\beta$-glycerophosphate ($\beta$-GP) and calcium acetate (CA), which made it possible to obtain a substrate of modified titanium coated by a titanium oxide layer containing Ca and P ions, elements that replace hydroxyapatite, a mineral in which nearly the totality of the calcium present in bones is stored. This work opened the way for subsequent developments, which have been focused on variations and implementations of the ASD technique for the surface modification of metal substrates. Document US2014/021055 describes, for example, a substrate of a metal selected in the group consisting of titanium, tantalum, titanium alloys and tantalum alloys, modified by means of the ASD technique. On its surface the substrate has a microporous, nanorough layer of the oxide of the same metal forming the substrate, enriched with Ca, P, Si, Na, and at least one metal selected from Ag and Ga as antibacterial agents. Document US20070191944, on the other hand, describes a method for coating an implant, such as, for example, a medical implant, which consists in subjecting a titanium surface to an anodic spark deposition (ASD) treatment with the aim of increasing its antioxidant activity. In some embodiments described in that document, the surface of the implant, after the ASD treatment, can comprise titanium oxide which, in turn, can comprise at least one metal such as, for example, barium and/or strontium.

Although the technologies described in US2014/021055 and US20070191944 represent an improvement over the method of Ishizawa et al., neither of these prior art documents addresses the problem of obtaining a substrate that exhibits antibacterial and osteointegrative properties simultaneously.

Thus, in the sector there remains a need to provide an orthopaedic device with antibacterial properties whose surface morphology is as similar as possible to the one with which cells normally interact, in order to obtain a positive interaction of the cells with the implanted device. To date, in fact, there are no available substrates obtained with the ASD technique which simultaneously possess both a high osteointegrative activity and antibacterial properties, since the surface treatments of the substrate are normally aimed at limiting the adhesion or proliferation of bacteria, but show to possess little or even no osteointegrative activity, given that in the majority of cases they prove to be toxic for the eukaryotic cells of the host tissue or lead to the formation of scarcely stable implants.

The present invention solves the problems of the prior art by providing a metal substrate and a prosthesis or a surgical implant comprising or, preferably, entirely produced with said substrate, with suitably modified morphological and chemical characteristics capable of enhancing osteointegration and simultaneously addressing the problem of preventing the infections associated with prosthetic implantology interventions, preferably orthopaedic prosthetic implantology. A further object of the present invention is to provide a process for modifying the surface morphology and chemistry of metal substrates by imparting to them a structure that is adapted to interact in an optimal manner with biological tissues and simultaneously endowing them with antibacterial properties. The objective of the invention is therefore to provide, by means of the process developed by the Applicant, a biomimetic treatment of metal substrates that favours the osteointegration of orthopaedic prostheses with the patient's bone tissue, thus ensuring the stability and functionality of the implant, said process being moreover highly reliable and relatively easy to provide at competitive costs. Finally, the subject matter of the present invention further relates to a prosthesis or an implant which comprises or is completely produced with said metal substrate modified by means of an ASD treatment and can be effectively used in the prevention of bacterial colonisation, the reduction of bacterial biofilm adhesion or the promotion of osteointegration in implantology operations, preferably orthopaedic implantology.

SUMMARY OF THE INVENTION

The present invention relates to a substrate of a metal, preferably titanium or a titanium alloy having at least one surface coated with an oxide layer of the metal, said surface being modified and enriched with Ca, P, Ga, Sr and, optionally, Ag ions by means of a morphological and chemical modification of said oxide layer of the metal with the anodic s spark deposition (ASD) technique.

The present invention also relates to a process for preparing said substrate of a metal, comprising the steps of:
(i) making up an aqueous solution comprising a Ga salt and a chelating agent (solution A); said solution optionally also comprising a salt of Ag (solution A'); and an aqueous solution comprising an Sr salt, a phosphate and a calcium salt (solution B);
(ii) mixing solution A (or solution A') with solution B to obtain an electrolytic solution;
(iii) providing a substrate of a metal, preferably titanium or a titanium alloy;
(iv) optionally pre-treating at least one surface of the substrate of step (iii) until obtaining a surface with a modified morphology;
(v) providing an electrolytic cell comprising a receptacle containing the electrolytic solution obtained in step (ii), the substrate of step (iii) or, optionally, the substrate obtained in step (iv) and a cathode;
(vi) connecting the substrate and the cathode respectively to the positive and negative poles of the cell and proceeding to treat the substrate by anodic spark deposition (ASD). Finally, the present invention also relates to a prosthesis and a surgical implant comprising or preferably entirely produced with said substrate as well as the use thereof for the prevention of bacterial colonisation, the reduction of bacterial biofilm adhesion or the promotion of osteointegration in implantology operations, preferably orthopaedic implantology.

DETAILED DESCRIPTION OF THE INVENTION

Figure 1:
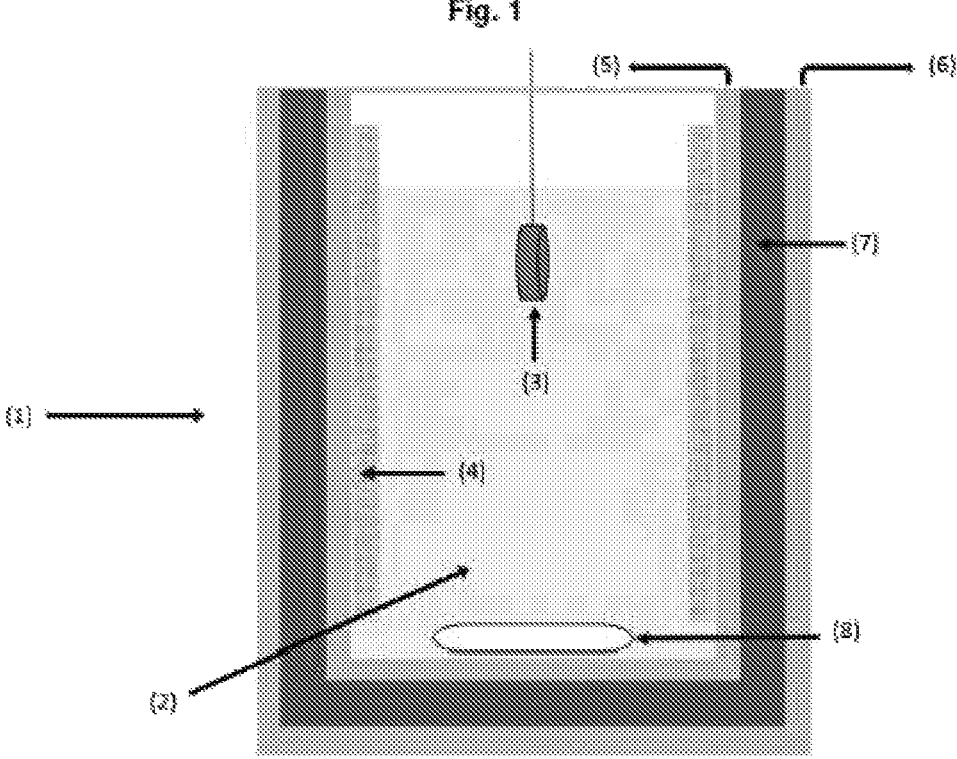
FIG. 1 shows a schematic representation of the electrolytic cell used in the process for preparing the substrate with antibacterial and osteointegrative properties according to the present invention.

For the purposes of the present invention, the expression "passivation layer" refers to the oxide layer that coats the surface of a metal and is formed, when a metal surface is exposed to air, as a result of the phenomenon of passivation. Therefore, for the purposes of the present invention, "passivated metal" means a metal having at least one surface coated by said passivation layer.

The "anodic spark deposition" (ASO) technique is also called MAO (microarc oxidation) or PEO (plasma electrolytic oxidation).

"Morphological and chemical modification of the oxide layer of the metal" means, for the purposes of the present invention, a modification, by anodic spark deposition (ASD), of the oxide layer, also referred to as "passivation layer", which is already present on the surface of a substrate of a metal, preferably titanium or alloys thereof, before treatment with the ASD technique. Therefore, this expression means the following modifications: the thickening of said oxide layer (i.e. passivation layer already present on said surface before the treatment with the ASD technique and the formation of microporosities, as well as the enrichment of said layer with chemical agents and species, such as, for example, Ca, P, Ga, Sr and, optionally, Ag ions.

Alternatively, if said surface of a substrate of a metal does not have a passivation layer, for example following a pickling treatment, the expression "morphological and chemical modification of the oxide layer of the metal" refers, for the purposes of the present invention, to the modification, by means of a treatment with the anodic spark deposition technique, of the oxide layer that is formed simultaneously with said treatment (also called "neo-formed" oxide layer). In this case, the expression therefore also means the following modifications: the formation of microporosities on the "neo-formed" oxide layer, as well as the simultaneous thickening and enrichment of said layer with chemical agents and species, such as, for example, Ca, P, Ga, Sr and, optionally, Ag ions.

For the purposes of the present invention, the expressions "surface enriched with Ca, P, Ga, Sr and, optionally, Ag" or the like and "oxide layer of the metal enriched with Ca, P, Ga, Sr and, optionally, Ag" or the like are to be understood as analogous, said surface being coated with said oxide layer of the metal.

For the purposes of the present invention, the terms "Ca ion", "Ca", "calcium ion", and "calcium" are to be understood as perfectly interchangeable synonyms indicating the element calcium in the oxidation state +2 (that is, the $Ca^{2+}$ ion).

For the purposes of the present invention, the terms "P ion", "P", "phosphorus ion", and "phosphorus" are to be understood as perfectly interchangeable synonyms indicating the element phosphorus in the oxidation state +5 (that is, the $P^{5+}$ ion).

For the purposes of the present invention, the terms "ion Ga", "Ga", "gallium ion", and "gallium" are to be understood as perfectly interchangeable synonyms indicating the element gallium in the oxidation state +3 (that is, the $Ga^{3+}$ ion).

For the purposes of the present invention, the terms "Sr ion", "Sr", "strontium ion", and "strontium" are to be understood as perfectly interchangeable synonyms indicating the element strontium in the oxidation state +2 (that is, the $Sr^{2+}$ ion).

For the purposes of the present invention, the terms "Ag ion", "Ag" "silver ion", and "silver" are to be understood as perfectly interchangeable synonyms indicating the element silver in the oxidation state +1 (that is, the $Ag^+$ ion).

For the purposes of the present invention, the term "titanium oxide" is to be considered a perfectly interchangeable synonym of "titanium oxide (IV)" or "titanium dioxide", that is, the chemical compound identified by the chemical formula $TiO_2$.

The present invention relates to a substrate of a metal having at least one surface coated with an oxide layer of the metal, wherein said coated surface is modified and enriched with Ca, P, Ga and Sr ions by means of a morphological and chemical modification of said oxide layer of the metal with the anodic spark deposition (ASD) technique.

In one embodiment of the invention, said coated surface is modified and further enriched with the Ag ion.

According to this embodiment, therefore, said substrate of a metal has at least one surface coated with an oxide layer of the metal, wherein said coated surface is modified and enriched with Ca, P, Ga and Sr ions, and, furthermore, Ag ions, by means of a morphological and chemical modification of said oxide layer of the metal with the anodic spark deposition (ASD) technique.

For the purposes of the present invention, the expressions "[further] enriched with the Ag ion" and "[further] enriched with Ag ions" are used as synonyms.

Advantageously, the substrate according to the present invention exhibits considerable antibacterial and osteointegration properties, which derive from the morphological and chemical modification that the at least one surface of the substrate of a metal undergoes as a result of the treatment with the ASD technique.

Preferably, said substrate is advantageous for applications in the medical-surgical realm, in particular in orthopaedic prosthetic implantology operations.

The metal of the substrate is preferably selected in the group consisting of titanium and a titanium alloy. In one embodiment, the substrate according to the present invention comprises a titanium alloy coated with a layer of metallic titanium, preferably by means of the plasma spray technique.

The titanium is preferably a non-alloyed titanium, i.e. pure metallic titanium without added alloy elements; more preferably said titanium is an ISO 5832-2 titanium (https://www.iso.org/standard/69907.html).

The titanium alloy is preferably selected from a $Ti_6Al_4V$ alloy and a $Ti_6Al_7Nb$ alloy, more preferably $Ti_6Al_7Nb$. In one embodiment, the titanium alloy is selected from a $Ti_6Al_4V$ ISO 5832-3 alloy (https://www.iso.org/standard/66637.html) and a $Ti_6Al_7Nb$ ISO 5832-11 alloy (https://www.iso.org/standard/21973.html), preferably $Ti_6Al_7Nb$ ISO 5832-11.

In a preferred embodiment of the invention, before the treatment with the ASD technique, the at least one surface of the substrate of a metal is coated by a passivation layer. Said passivation layer is an oxide layer of the metal itself; it is preferably a layer of titanium dioxide.

In one embodiment of the invention, the at least one surface of the substrate coated with said passivation layer is a hydrophilic surface, whose characteristics of hydrophilicity are also maintained following the morphological and chemical modification obtained with the treatment by anodic spark deposition (ASD).

In another embodiment of the invention, before the treatment with the ASD technique, the at least one surface of the substrate is not coated by a passivation layer. In this case the treatment by anodic spark deposition permits the formation of an oxide layer on said at least one surface and the simultaneous morphological and chemical modification of said "neo-formed" oxide layer. The substrate thus obtained has at least one surface coated with an oxide layer of the metal itself, said surface being a hydrophilic surface.

The hydrophilicity of the surface of the final substrate, i.e. following treatment with the anodic spark deposition technique, which is linked to the wettability of the substrate itself, proves to be advantageous for the purposes of the present invention, since the bacterial strains involved in infections in the medical-surgical realm, in particular in the case of orthopaedic implantology operations, belong to the strains *Staphylococcus aureus* or *Staphylococcus epidermidis*, which are typically hydrophobic and thus adhere and proliferate mainly on hydrophobic surfaces.

The oxide layer of the metal, preferably of titanium dioxide, which coats the at least one surface of the substrate following treatment with the anodic spark deposition technique according to the present invention, has a thickness comprised from 1 to 20 μm, preferably from 2 to 15 μm, even more preferably from 3 to 8 μm.

In the embodiment of the invention wherein the at least one surface of the substrate of a metal is coated by a passivation layer, the thickness of the oxide layer obtained following treatment with the anodic spark deposition technique is greater than the thickness of the oxide of the metal, preferably of titanium dioxide, of said passivation layer present on the substrate (equal to about 5 nm), precisely because of the modification of the surface of the substrate coated by that layer, a modification that occurs following the ASD treatment, which causes the thickness of said oxide of the passivation layer to grow (from a few nanometres to several micrometres, as indicated above) and, at the same time, transforms the surface of the substrate from compact and smooth to microporous. The thickening of the oxide layer also has the advantage of reducing the passivity current in saline solution and preventing the release of ions of the metal of the substrate, preferably titanium, and the dissolution of the metal itself or of alloy elements, preferably titanium or a titanium alloy, in bodily fluids. In applications in the medical-surgical realm, in particular orthopaedic prosthetic implantology operations, this prevents the substrate of the invention from being able to cause local irritations in tissues or, in the long term, sensitisation in the patient to the metal ions released.

In both embodiments, i.e. both in the case where, before the treatment with the ASD technique, the at least one surface of the substrate of a metal is coated by a passivation layer and in the case where said at least one surface has no passivation layer, following the ASD treatment the oxide layer of the metal, preferably of titanium dioxide, which coats the at least one surface of the substrate of a metal according to the present invention, is a microporous layer characterised by having pores of a size, as measured by scanning electron microscope (SEM) analysis, comprised from 50 nm to 5 µm, preferably from 100 nm to 3 µm. Said pores are homogeneously distributed in the oxide layer.

According to the present invention, the porous structure of the oxide layer coating the at least one surface of the substrate following treatment with the anodic spark deposition technique makes it possible to positively influence the adhesion, proliferation and differentiation of bone cells (osteoblasts), to increase contact with the bone in "in vivo" applications and thus to improve the mechanical stability of the implant in general.

Furthermore, the ASD treatment enables the incorporation, into the oxide layer, of the doping agents initially present in the electrolytic solution used for the treatment, thanks to local phenomena of melting and solidification of the oxide layer itself which are induced by the high temperatures and plasma microdischarges (sparks) that develop with the ASO treatment. Simultaneously, as a result of such melting phenomena (also called micromelting), there is also the formation of a controlled, homogeneously distributed porosity.

Advantageously, the morphological characteristics in terms of thickening and porosity ensure that the oxide layer will be firmly anchored to the substrate after the treatment with the anodic spark deposition technique; in fact, in the event of excessively large thicknesses there could be, for example, phenomena of delamination of the oxide layer, with a consequent impairment of the performance and success of the implant.

Advantageously, the morphological characteristics in terms of thickening and porosity are concomitantly and simultaneously imparted by the ASO treatment to the oxide layer of the metal, preferably of titanium dioxide, which coats the at least one surface of the substrate according to the present invention.

In addition to such morphological modifications, the at least one surface of the substrate of a metal coated with an oxide layer of the metal itself according to the present invention is enriched with Ca, P, Ga, Sr, and, optionally, Ag ions.

According to one embodiment, the at least one surface of the substrate of a metal coated with an oxide layer of the metal itself according to the present invention is enriched with Ca, P, Ga and Sr ions.

According to another embodiment, the at least one surface of the substrate of a metal coated with an oxide layer of the metal itself according to the present invention is enriched with Ca, P, Ga, Ag and Sr ions.

In both embodiments, this enrichment is due to the chemical modification of said oxide layer which takes place simultaneously with the morphological modification in the ASD treatment.

Said ions derive from the ions present in the electrolytic solution used in the ASO technique and are incorporated into the oxide layer during the treatment.

In one embodiment of the invention, following treatment with the anodic spark deposition technique, the substrate of a metal, preferably titanium or an alloy thereof, has at least one surface coated with an oxide layer of the metal, preferably of titanium dioxide, wherein said layer is enriched with an amount of Ga comprised from 0.01 to 30 µg/cm², preferably from 2 to 30 µg/cm², more preferably from 0.02 to 8 µg/cm², more preferably from 3 to 8 µg/cm², even more preferably from 0.03 to 6 µg/cm², even more preferably from 4 to 6 µg/cm².

In one embodiment of the invention, following treatment with the anodic spark deposition technique, the substrate of a metal, preferably titanium or an alloy thereof, has at least one surface coated with an oxide layer of the metal, preferably of titanium dioxide, wherein said layer is enriched with an amount of Sr comprised from 10 to 250 µg/cm², preferably from 50 to 350 µg/cm², more preferably from 30 to 120 µg/cm², more preferably from 70 to 250 µg/cm². even more preferably from 40 to 70 µg/cm², even more preferably from 100 to 150 µg/cm².

In one embodiment of the invention, following treatment with the anodic spark deposition technique, the substrate of a metal, preferably titanium or an alloy thereof, has at least one surface coated with an oxide layer of the metal, preferably of titanium dioxide, wherein said layer is enriched:

with an amount of Ga comprised from 0.01 to 30 µg/cm², preferably from 2 to 30 µg/cm², more preferably from 0.02 to 8 µg/cm², more preferably from 3 to 8 µg/cm², even more preferably from 0.03 to 6 µg/cm², even more preferably from 4 to 6 µg/cm²; and with an amount of Sr comprised from 10 to 250 µg/cm², preferably from 50 to 350 µg/cm², more preferably from 30 to 120 µg/cm², more preferably from 70 to 250 µg/cm², even more preferably from 40 to 70 µg/cm², even more preferably from 100 to 150 µg/cm².

In one embodiment of the invention wherein said coated surface is modified and further enriched with the Ag ion, said layer is enriched with an amount of Ag comprised from 0.05 to 10 µg/cm², preferably from 0.10 to 5 µg/cm². more preferably from 0.30 to 2 µg/cm².

According to this embodiment, said layer is enriched preferably with an amount of Ga comprised from 0.01 to 30 µg/cm², preferably from 2 to 30 µg/cm², more preferably from 0.02 to 8 µg/cm², more preferably from 3 to 8 µg/cm², even more preferably from 0.03 to 6 µg/cm², even more preferably from 4 to 6 µg/cm² and, preferably, with an amount of Sr comprised from 10 to 250 µg/cm², preferably from 50 to 350 µg/cm², more preferably from 30 to 120 µg/cm², more preferably from 70 to 250 µg/cm², even more preferably from 40 to 70 µg/cm², even more preferably from 100 to 150 µg/cm².

Advantageously, the presence of Ga and Sr ions, or Ga, Ag and Sr ions, simultaneously with the presence of Ca and P ions (useful in promoting direct contact between the bone and the implant without the interposition of fibrous tissue), and above all with the presence of the particular morphological characteristics in terms of thickness and porosity described above, imparts to the substrate of the present invention not only excellent antibacterial properties but also excellent osteointegration.

These properties are due to the synergistic effect of the combination of morphological and chemical characteristics of the modified oxide layer.

In particular, without wishing to be bound by a specific theory, it is possible to maintain that the ASO process, precisely thanks to the simultaneous formation of a controlled porosity and the incorporation into the oxide layer of Ga and Sr ions, or Ga, Ag and Sr ions, the former (i.e. Ga ions or Ga and Ag ions) known for their antibacterial properties, whereas the latter (i.e. Sr ions) are known for their osteointegrative properties, contributes to enhancing osteointegration and antibacterial properties, while enabling the adhesion, proliferation and differentiation of bone cells (osteoblasts)

In particular, Sr ions—by activating a receptor sensitive to calcium, CaSR—further promote the replication and differentiation of osteoblasts while simultaneously inhibiting osteoclastic activity, thus favouring the formation of new bone matrix.

The possibility of having Ga and Sr ion co-doping or Ga, Ag and Sr multiple ion doping within a layer with morphologically favourable characteristics as regards thickness, wettability and porosity ensures that the substrate of the present invention simultaneously possesses the desired antibacterial and osteointegrative properties.

Furthermore, as demonstrated in the Examples section, the presence of Ga ions alone, or of Ga and Ag ions alone, though it may assure an excellent antibacterial activity, even superior to that obtainable with an Sr and Ga ion co-doping or with a Ga, Ag and Sr multiple ion doping, would not, however, guarantee the desired osteointegrative properties.

Similarly, the sole presence of Sr ions in the oxide layer, though it may favour an osteointegration that is far greater, would not, however, enable an adequate antibacterial action.

As also demonstrated by the experimental tests illustrated in the Examples section, the present invention, by exploiting the morphological and chemical modifications of the oxide layer obtained by means of the ASD treatment, enables an optimal balance to be obtained between the antibacterial and osteointegrative action. This is due to the simultaneous presence of gallium and strontium (and, optionally Ag) ions and the characteristics of porosity, wettability (i.e. hydrophilicity) and thickness of the oxide layer coating the surface of the substrate, whose different contributions synergistically impart to the substrate the antibacterial and osteointegrative properties which are desired for the purposes of the present invention.

The hydrophilicity of the surface of the substrate is further advantageous for the purposes of the present invention since, as mentioned previously, the bacterial strains involved in infections in the medical-surgical realm, in particular in the case of orthopaedic implantology operations, belong to the strains *S. aureus* or *S. epidermidis*, which are typically hydrophobic and thus adhere and proliferate mainly on hydrophobic surfaces.

The present invention also relates to a process for preparing a substrate of a metal, preferably titanium or a titanium alloy, having at least one surface coated with an oxide layer of the metal, wherein said coated surface is modified and enriched with Ca, P, Ga and Sr ions by means of a morphological and chemical modification of said oxide layer of the metal with the anodic spark deposition (ASD) technique, said process comprising the steps of:

(i) making up an aqueous solution comprising a Ga salt and a chelating agent (solution A) and an aqueous solution comprising an Sr salt, a phosphate and a calcium salt (solution B);

(ii) mixing solution A with solution B to obtain an electrolytic solution;

(iii) providing a substrate of a metal, preferably titanium or a titanium alloy;

(iv) optionally pre-treating at least one surface of the substrate of step (iii) until obtaining a surface with a modified morphology;

(v) providing an electrolytic cell comprising a receptacle (1) containing the electrolytic solution (2) obtained in step (ii), the substrate (3) of step (iii) or, optionally, the substrate (3) obtained in step (iv) and a cathode;

(vi) connecting the substrate and the cathode respectively to the positive and negative poles of the cell and proceeding to treat the substrate by anodic spark deposition (ASD). The present invention also relates to a process for preparing a substrate of a metal, preferably titanium or a titanium alloy, having at least one surface coated with an oxide layer of the metal, wherein said coated surface is modified and enriched with Ca, P, Ga and Sr ions, and, furthermore, Ag ions, by means of a morphological and chemical modification of said oxide layer of the metal with the anodic spark deposition (ASD) technique, said process comprising the steps of:

(i) making up an aqueous solution comprising a Ga salt, an Ag salt and a chelating agent (solution A') and an aqueous solution comprising an Sr salt, a phosphate and a calcium salt (solution B);

(ii) mixing solution A' with solution B to obtain an electrolytic solution;

(iii) providing a substrate of a metal, preferably titanium or a titanium alloy;

(iv) optionally pre-treating at least one surface of the substrate of step (iii) until obtaining a surface with a modified morphology;

(v) providing an electrolytic cell comprising a receptacle (1) containing the electrolytic solution (2) obtained in step (ii), the substrate (3) of step (iii) or, optionally the substrate (3) obtained in step (iv) and a cathode;

(vi) connecting the substrate and the cathode respectively to the positive and negative poles of the cell and proceeding to treat the substrate by anodic spark deposition (ASD).

In one embodiment of the invention, the electrolytic solution obtained in step (i) comprises said Ga salt at a concentration comprised from 0.001 to 0.008 M, preferably from 0.002 to 0.004 M.

In the embodiment wherein the solution prepared in step (i) further comprises an Ag salt (solution A'), the electrolytic solution obtained in step (ii) comprises said Ga salt at a concentration comprised from 0.0001 to 0.002 M, preferably from 0.0003 to 0.001 M, and said Ag salt at a concentration comprised from 0.001 to 0.015 M, preferably from 0.002 to 0.010 M.

Said Ga salt is preferably selected in the group consisting of: gallium nitrate ($Ga(NO_3)_3$), gallium nitrate hydrate ($Ga(NO_3)_3*H_2O$) and gallium acetate $Ga(C_2H_3O_2)_3$.

Said Ag salt is preferably selected in the group consisting of: silver nitrate ($AgNO_3$) and silver acetate ($AgC_2H_3O_2$).

The electrolytic solution obtained in step (ii) preferably comprises said Sr salt at a concentration comprised from 0.01 to 0.3 M, preferably from 0.05 to 0.15 M. Said Sr salt is preferably selected in the group consisting of: strontium acetate ($(CH_3CO_2)_2Sr$) and strontium nitrate $Sr(NO_3)_2$.

The electrolytic solution obtained in step (ii) preferably comprises said chelating agent at a concentration comprised from 0.002 to 0.01 M, preferably from 0.004 to 0.008 M, said phosphate at a concentration comprised from 0.02 to 0.2 M, preferably from 0.03 to 0.05 M and said calcium salt at a concentration comprised from 0.05 to 0.6 M, preferably from 0.2 to 0.3 M.

Said chelating agent is preferably selected in the group consisting of: L-cysteine ($HSCH_2CH(NH_2)CO_2H$), oxalic acid and ethylenediaminetetraacetic acid (EDTA).

Said phosphate is preferably β-glycerophosphate disodium salt pentahydrate (β-GP) ($C_3H_7Na_2O_6P*5H_2O$).

Said calcium salt is preferably calcium acetate monohydrate (CA) ($C_4H_6CaO_4*H_2O$).

The substrate of a metal provided in step (iii) of the process according to the present invention preferably has at least one surface that may or may not be coated by a passivation layer, said passivation layer being an oxide layer of the metal itself. In other words, step (iii) of the process according to the present invention envisages providing a substrate of a metal wherein said metal is preferably passivated or non-passivated.

In one embodiment of the invention, the process for preparing a substrate of a metal, preferably titanium or a titanium alloy, having at least one surface coated with an oxide layer of the metal itself, wherein said coated surface is modified and enriched with Ca, P, Ga and Sr ions by means of a morphological and chemical modification of said oxide layer with the anodic spark deposition (ASD) technique, comprises the steps of:

(i) making up an aqueous solution comprising: a Ga salt at a concentration comprised from 0.001 to 0.008 M, preferably from 0.002 to 0.004 M, and a chelating agent at a concentration comprised from 0.002 to 0.01 M, preferably from 0.004 to 0.008 M (solution A);

and an aqueous solution comprising: an Sr salt at a concentration comprised from 0.01 to 0.3 M, preferably from 0.05 to 0.15 M, a phosphate at a concentration comprised from 0.02 to 0.2 M, preferably from 0.03 to 0.05 M, and a calcium salt at a concentration comprised from 0.05 to 0.6 M, preferably from 0.2 to 0.3 M (solution B);

(ii) mixing solution A with solution B to obtain an electrolytic solution;

(iii) providing a substrate of a metal, preferably titanium or a titanium alloy, said metal preferably being passivated or non-passivated;

(iv) optionally pre-treating at least one surface of the substrate of step (iii) until obtaining a surface with a modified morphology;

(v) providing an electrolytic cell comprising a receptacle (1) containing the electrolytic solution (2) obtained in step (ii), the substrate (3) of step (iii) or, optionally, the substrate (3) obtained in step (iv) and a cathode (vi) connecting the substrate and the cathode respectively to the positive and negative poles of the cell and proceeding to treat the substrate by anodic spark deposition (ASD).

In a preferred embodiment of the invention, the process for preparing a substrate of a metal, preferably titanium or a titanium alloy, having at least one surface coated with an oxide layer of the metal itself, wherein said coated surface is modified and enriched with Ca, P, Ga and Sr ions by means of a morphological and chemical modification of said oxide layer with the anodic spark deposition (ASD) technique comprises the steps of:

(i) making up an aqueous solution comprising gallium nitrate hydrate ($Ga(NO_3)_3*H_2O$) at a concentration comprised from 0.001 to 0.008, preferably from 0.002 to 0.004 M and L-cysteine ($HSCH_2CH(NH_2)CO_2H$) at a concentration comprised from 0.002 to 0.01 M, preferably from 0.004 to 0.008 M (solution A) and an aqueous solution comprising strontium acetate ($(CH_3CO_2)_2Sr$) at a concentration comprised from 0.01 to 0.3 M, preferably from 0.05 to 0.15 M, 3-glycerophosphate disodium salt pentahydrate (β-GP) ($C_3H_7Na_2O_6P*5H_2O$) at a concentration comprised from 0.02 to 0.2, preferably from 0.03 to 0.05 M, and calcium acetate monohydrate (CA) ($C_4H_6CaO_4*H_2O$) at a concentration comprised from 0.05 to 0.6 M, preferably from 0.2 to 0.3 M (solution B);

(ii) mixing solution A with solution B to obtain an electrolytic solution;

(iii) providing a substrate of a metal, preferably titanium or a titanium alloy, said metal preferably being passivated or non-passivated;

(iv) optionally pre-treating at least one surface of the substrate of step (iii) until obtaining a surface with a modified morphology;

(v) providing an electrolytic cell comprising a receptacle (1) containing the electrolytic solution (2) obtained in step (ii), the substrate (3) of step (iii) or, optionally, the substrate (3) obtained in step (iv) and a cathode (vi) connecting the substrate and the cathode respectively to the positive and negative poles of the cell and proceeding to treat the substrate by anodic spark deposition (ASD).

In one embodiment of the invention, the process for preparing a substrate of a metal, preferably titanium or a titanium alloy, having at least one surface coated with an oxide layer of the metal itself, wherein said coated surface is modified and enriched with Ca, P, Ga and Sr ions, and, furthermore, Ag ions by means of a morphological and chemical modification of said oxide layer with the anodic spark deposition (ASD) technique, comprises the steps of:

(i) making up an aqueous solution comprising: a Ga salt at a concentration comprised from 0.0001 to 0.002 M, preferably from 0.0003 to 0.001 M, an Ag salt at a concentration comprised from 0.001 to 0.015 M, preferably from 0.002 to 0.010 M, and a chelating agent at a concentration comprised from 0.002 to 0.01 M, preferably from 0.004 to 0.008 M (solution A');

and an aqueous solution comprising: an Sr salt at a concentration comprised from 0.01 to 0.3 M, preferably from 0.05 to 0.15 M, a phosphate at a concentration comprised from 0.02 to 0.2 M, preferably from 0.03 to 0.05 M, and a calcium salt at a concentration comprised from 0.05 to 0.6 M, preferably from 0.2 to 0.3 M (solution B);

(ii) mixing solution A' with solution B to obtain an electrolytic solution;

(iii) providing a substrate of a metal, preferably titanium or a titanium alloy, said metal preferably being passivated or non-passivated;

(iv) optionally pre-treating at least one surface of the substrate of step (iii) until obtaining a surface with a modified morphology;

(v) providing an electrolytic cell comprising a receptacle (1) containing the electrolytic solution (2) obtained in step (ii), the substrate (3) of step (iii) or, optionally, the substrate (3) obtained in step (iv) and a cathode;

(vi) connecting the substrate and the cathode respectively to the positive and negative poles of the cell and proceeding to treat the substrate by anodic spark deposition (ASD).

In a preferred embodiment of the invention, the process for preparing a substrate of a metal, preferably titanium or a titanium alloy, having at least one surface coated with an oxide layer of the metal itself, wherein said coated surface is modified and enriched with Ca, P, Ga and Sr ions, and, furthermore, Ag ions by means of a morphological and chemical modification of said oxide layer with the anodic spark deposition (ASD) technique comprises the steps of:

(i) making up an aqueous solution comprising gallium nitrate hydrate $(Ga(NO_3)_3*H_2O)$ at a concentration comprised from 0.0001 to 0.002 M, preferably from 0.0003 to 0.001 M. silver nitrate $(Ag(NO_3))$ at a concentration comprised from 0.001 to 0.015 M, preferably from 0.002 to 0.010 M, and L-cysteine $(HSCH_2CH(NH_2)CO_2H)$ at a concentration comprised from 0.002 to 0.01 M, preferably from 0.004 to 0.008 M (solution A'); and an aqueous solution comprising strontium acetate $((CH_3CO_2)_2Sr)$ at a concentration comprised from 0.01 to 0.3 M, preferably from 0.05 to 0.15 M. $\beta$-glycerophosphate disodium salt pentahydrate ($\beta$-GP) $(C_3H_7Na_2O_6P*5H_2O)$ at a concentration comprised from 0.02 to 0.2, preferably from 0.03 to 0.05 M, and calcium acetate monohydrate (CA) $(C_4H_6CaO_4*H_2O)$ at a concentration comprised from 0.05 to 0.6 M, preferably from 0.2 to 0.3 M (solution B);

(ii) mixing solution A' with solution B to obtain an electrolytic solution; (iii) providing a substrate of a metal, preferably titanium or a titanium alloy, said metal preferably being passivated or non-passivated;

(iv) optionally pre-treating at least one surface of the substrate of step (iii) until obtaining a surface with a modified morphology;

(v) providing an electrolytic cell comprising a receptacle (1) containing the electrolytic solution (2) obtained in step (ii), the substrate (3) of step (iii) or, optionally, the substrate (3) obtained in step (iv) and a cathode (vi) connecting the substrate and the cathode respectively to the positive and negative poles of the cell and proceeding to treat the substrate by anodic spark deposition (ASD).

Advantageously, the concentrations of the components of the electrolytic solution are such as to avoid spontaneous precipitation of the elements in the solution, in order to permit the reuse thereof (with a consequent economic advantage). Furthermore, these concentrations are such as to take account of the fact that, when working at higher concentrations, the ASD treatment could give rise to coatings that have breaks or discontinuities in the oxide layer, in particular at the interface between the oxide and the substrate, thus impairing performance in terms of adhesion to bone tissues and consequently also reducing osteointegration.

In an alternative embodiment of the invention, the substrate of a metal of step (iii) is preferably a substrate obtained by means of the "additive manufacturing" technique.

Advantageously, this technique makes it possible to obtain a substrate that has, on at least one surface, preferably on all the surfaces of said substrate, macroporous structures with open or closed pores, these being structures which further favour performance in terms of long-term osteointegration of the substrate of the invention. With regard to step (iv), the pre-treatment of the at least one surface of the substrate enables the at least one surface of the substrate to be modified from a morphological viewpoint.

Said pre-treatment is preferably carried out by means of a surface modification technique selected in the group consisting of: sandblasting, coating with metallic titanium by plasma spraying, coating with titanium microspheres sintered onto the surface, coating with titanium fragments, coating with rough or porous titanium and combinations thereof.

Without wishing to be bound by a specific theory, the Applicant has found that said pre-treatment makes it possible to increase the roughness of the at least one surface of the substrate and thus obtain a substrate exhibiting a surface roughening, this characteristic enabling performance to be further improved in terms of long-term osteointegration of the substrate of the invention.

With regard to step (v), said cathode is preferably a cathode made of metallic or non-metallic material; more preferably, said cathode is a metallic cathode, even more preferably, said cathode is a cathode made of titanium.

In a preferred embodiment of the invention, the receptacle (1) of the electrolytic cell of step (v) is a double-walled refrigerating receptacle comprising a liquid refrigerant (7) in the space interposed between the inner wall (5) and the outer wall (6).

In a preferred embodiment of the invention, the metallic cathode contained inside the electrolytic cell of step (v) is a metal mesh (4), preferably made of titanium, preferably subjected to a pickling process, applied as a coating of the inner walls (5) of the receptacle (1).

In one embodiment, the process according to the present invention envisages that the step of treatment by anodic spark deposition (step (vi)) is carried out at a temperature comprised from $-5$ to $+5°$ C., preferably at a temperature comprised from $-1$ to $+1°$ C.

This temperature serves to avoid a possible inhibition of the current between the anode and cathode of the circuit. Furthermore, this temperature also plays a role in ensuring that the capacity of adhesion between the oxide layer and the substrate is maintained, a capacity which would otherwise decrease at higher temperatures.

In one embodiment of the invention, the process for preparing a substrate as previously described, that is, a substrate of a metal, preferably titanium or a titanium alloy, having at least one surface coated with an oxide layer of the metal, wherein said coated surface is modified and enriched with Ca, P, Ga, Sr and, optionally, Ag ions by means of a morphological and chemical modification of said oxide layer of the metal with the anodic spark deposition (ASD) technique, envisages that the step of treatment by means of said ASD technique is performed working with direct current at a first current density comprised from 5 to 50 mA/cm$^2$, preferably from 10 to 30 mA/cm$^2$, with a potential that increases independently up to a value comprised from 210 to 330 V, preferably from 260 to 310 V, for a period of time necessary to reach that final potential value, and at a second current density comprised from 50% to 5% of the value of the first current density.

In one embodiment, the process for preparing a substrate as previously described envisages that the step of treatment by means of the ASD technique is performed working with pulsed current. The possibility of being able to work with pulsed current not only brings advantages in terms of homogeneity of the treatment, but also makes it possible to obtain better control of the temperature inside the electrolytic cell as well as increasing the reproducibility of the process.

Advantageously, the process of the present invention makes it possible to obtain a substrate of a metal, preferably titanium or a titanium alloy, having at least one surface coated with an oxide layer of the metal, wherein said coated surface is modified and enriched with Ca, P, Ga, Sr, and, optionally, Ag ions by means of a morphological and chemical modification of said oxide layer of the metal with the anodic spark deposition (ASD) technique, with characteristics that are ideal for applications in the medical-surgical realm, such as, for example, in orthopaedic prosthetic implantology operations. The process of the present invention in fact makes it possible to modulate, simultaneously and in a single step, the morphological and chemical characteristics of the oxide layer coating the at least one surface of the treated substrate, thus enabling a substrate with both antibacterial and osteointegrative properties to be obtained.

The Applicant has demonstrated that the simultaneous presence of Ga and Sr or of Ga, Ag and Sr in the electrolytic solution obtained according to steps (i) and (ii) leads to an efficient co-doping (or multiple doping) of the oxide layer, since said ions are incorporated into the oxide layer during the ASD process.

Advantageously, thanks precisely to the simultaneous morphological and chemical modification of the oxide layer, it is possible to obtain a substrate with the desired antibacterial and osteointegrative properties.

In one embodiment of the invention, the pores formed by means of the ASD process can be loaded with ions, molecules and/or drugs which are then released, once introduced into the substrate of the present invention, within the patient's bone tissue.

Said loading of the pores formed by means of the process ASD with ions, molecules and/or drugs preferably takes place by immersing the substrate of the present invention in a solution containing said ions, molecules and/or drugs, such as, for example, antibiotics.

The present invention further relates to a prosthesis comprising the substrate as previously described.

In a preferred embodiment of the invention, said prosthesis is entirely produced with said substrate.

In one embodiment of the invention, said prosthesis is an orthopaedic prosthesis selected in the group consisting of: upper limb prostheses and lower limb prostheses.

Finally, the present invention also relates to a surgical implant comprising the substrate as previously described.

In a preferred embodiment of the invention said implant is entirely produced with said substrate.

In one embodiment of the invention, said implant is an orthopaedic implant selected in the group consisting of: hip prostheses, knee prostheses, shoulder and ankle joint prostheses, osteosynthesis means, intervertebral fusion cages, spinal prostheses, devices for filling bone lacunae and bone fixating systems for external fixators.

The subject matter of the present invention further relates to a prosthesis or a surgical implant as previously described for use in the prevention of bacterial colonisation, the reduction of bacterial biofilm adhesion or the promotion of osteointegration in implantology operations, preferably orthopaedic implantology.

Advantageously, in fact, the prosthesis or the surgical implant comprising or preferably entirely produced with the substrate of the present invention make it possible to combat bacterial adhesion and proliferation on the surfaces thereof without inducing any harmful effect on eukaryotic cells and at the same time they promote the adhesion, differentiation and growth of osteoblasts, thus enhancing osteointegration into the patient's bone tissue.

EXAMPLES

Example 1—Materials and Methods 1.1 Type of Samples

The samples used in the following experiments are disc-shaped samples with a diameter of 1 cm and thickness of 0.2 cm, made of titanium alloy $Ti_6Al_7Nb$ conforming to standard ISO 5832-3, supplied by the company Medacta International SA. The samples were subjected to a surface finishing pre-treatment by sandblasting with white corundum F 36 on one side of the sample. The samples thus obtained are indicated as "untreated" samples (NT).

1.2 ASD Treatment

A part of the samples (NT) obtained as previously described was subjected to the ASD treatment, whilst another part was stored in the "untreated" state in order to be able to conduct appropriate comparative experiments.

The electrolytic solutions used were prepared using an aqueous solution containing calcium acetate monohydrate (CA) and β-glycerophosphate disodium salt pentahydrate (β-GP) as described by Ishizawa et al. ("H. Ishizawa, "Formation and characterization of anodic titanium oxide films containing Ca and P", Journal of Biomedical Materials Research, Vol. 29, 6572 (1995)), modified by adding a solution containing a strontium salt as an element for favouring osteointegration and/or a solution containing a gallium salt as an antibacterial agent.

In order to prevent the precipitation of the gallium ions in the solution, L-cysteine was also added as a chelating agent for that ion.

The electrolytic solutions were prepared by joining two different solutions: the first containing gallium and L-cysteine (solution A), and the second containing the remaining elements (solution B). The reason for this preparation lies in the presence of the chelating agent, which must advantageously bind solely to the gallium and not to the other ions. Once chelation has taken place, solutions A and B can be combined to obtain the electrolytic solutions to be used in the ASD treatment.

The reagents present in the various electrolytic solutions, along with the associated specifications and the molarities used, are shown in the table below (Table 1):

TABLE 1

| Reagents | Chemical formula | Molecular weight (g/mol) | Molarity (M) |
|---|---|---|---|
| β-GP (Glycerophosphate disodium salt pentahydrate (Sigma-Aldrich, 50020) | $C_3H_7Na_2O_6P*5H_2O$ | 306.12 | 0.04 |
| Calcium acetate (CA) (Sigma-Aldrich, 25011) | $C_4H_6CaO_4*H_2O$ | 158.17 | 0.25 |
| Strontium acetate (Sigma-Aldrich, 388548) | $(CH_3CO_2)_2Sr$ | 205.71 | 0.05[a]/0.08[b]/0.12[c]/0.15[d] |
| Gallium nitrate (Sigma-Aldrich, S6506) | $Ga(NO_3)_3*H_2O$ | 225.74 | 0.002-0.004 |

TABLE 1-continued

| Reagents | Chemical formula | Molecular weight (g/mol) | Molarity (M) |
|---|---|---|---|
| L-cysteine (Sigma-Aldrich, W326305) | HSCH$_2$CH(NH$_2$)CO$_2$H | 121.16 | 0.006 |

As indicated in the table, the electrolytic solutions were tested by varying the concentration of strontium (a, b, c, d) in order to determine the best electrolytic solution for the purposes of the present invention.

The ASD treatment was performed in the galvanostatic mode; a voltage of 300 V and a current density of 20 mA/cm$^2$ were set.

For the treatment, irrespective of the ions present in the solution, the average anodisation time was approximately 5 minutes.

The experimental set up used entails preparing first of all an electrolytic cell as schematically illustrated in FIG. 1, comprising a double-walled receptacle in which the space interposed between the inner wall and the outer wall is occupied by a refrigerant liquid whose temperature is regulated by an automatic refrigerator (Julabo F32-HL refrigerated/heating circuit with a temperature range −35 to +200° C.). This enables the electrolytic solution contained inside the receptacle to gradually reach and maintain a constant temperature of 0±1° C. during the treatment. A magnetic stirrer is positioned on the bottom of the receptacle and produces a vortex that keeps the electrolytic solution under continuous stirring.

For the purpose of conducting experimental tests, the sample to be treated (i.e. the titanium alloy sample as previously described), which corresponds to the anode of the electrochemical circuit, was immersed in the solution. It was kept suspended thanks to a sample holder, likewise made of titanium, which was connected to the positive pole of the cell, whereas the negative pole was connected to a metal mesh, also made of titanium (previously subjected to a pickling process), which covers the inner walls of the receptacle and acts as the cathode. The instrument used for the treatment is a programmable DC current generator (N5772A, Agilent Technologies, Everett, WA, USA) with a full-scale value of 600 V and maximum current intensity of 2.4 A.

The samples obtained and subsequently characterised and used for the experiments described below are classified as:

"Ga" samples, obtained following the ASO treatment with electrolytic solutions as described in Table 1, in the absence of strontium ions;

"SrGa" samples, obtained following the ASO treatment with electrolytic solutions containing gallium and strontium ions, the latter present in different concentrations (see solutions a, b, c, d shown in Table 1).

Figure 2:
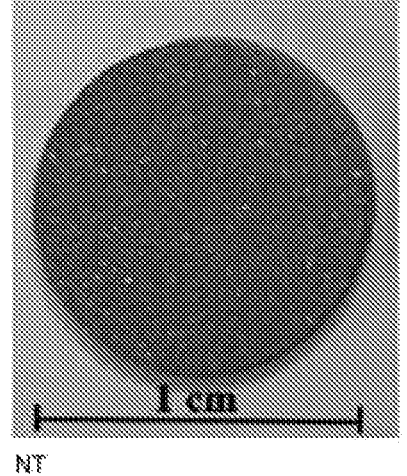
FIG. 2 contains a photo which shows a comparison, appreciable with the naked eye, between an untreated sample (NT) and an SrGa sample obtained following the ASD treatment with electrolytic solutions containing Ga and Sr ions, the latter present at a concentration of 0.08M, as per Example 1.
Figure 2:
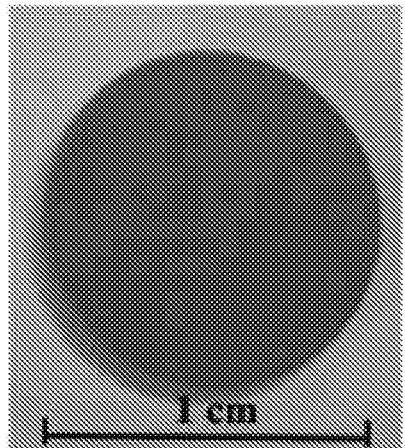

As shown in FIG. 2, it is possible to appreciate a change, which is also visible to the naked eye, in the surface of untreated samples (NT) versus the samples subjected to the ASD treatment, since the surface of the latter appears to take on specific colours.

1.3 Statistical Analysis

The statistical analyses were performed using GraphPad Prism 7.0 software; a p-value <0.05 was identified as the level of significance.

After the normal distribution of variance was verified, one-way ANOVA tests were performed, followed by appropriate post-hoc tests and Student's t-test for independent samples in order to measure the contact angle and cell and bacterial viability, as described in the Examples below.

Two-way ANOVA tests were performed for the microbiological and biological tests, as described in the Examples below (see, in particular, Examples 6 and 7).

Example 2—Chemical Characterisation 2.1 Inductively Coupled Plasma—Optical Emission Spectrometry (ICP-OES)

The chemical characterisation was carried out for the purpose of verifying and quantifying the presence of strontium and gallium ions incorporated into the titanium oxide layer coating the treated samples.

In particular, in order to verify the effectiveness of the method of the present invention as regards the incorporation of ions into the titanium oxide, a chemical characterisation by means of inductively coupled plasma—optical emission spectrometry (ICP-OES) was carried out. This type of analysis makes it possible to measure the concentration of the elements, in particular strontium and gallium, incorporated into the titanium oxide layer present on the surface of the sample, in terms of μg/cm$^2$.

The analyses were performed with a Perkin Elmer Optima 8300 spectrometer.

Figure 3:
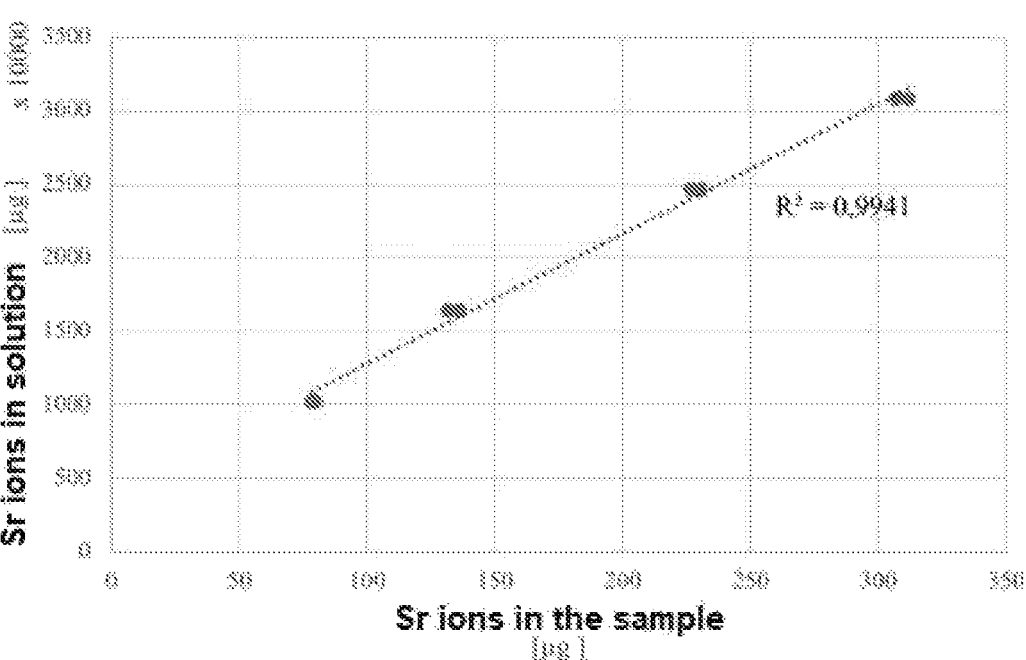
FIG. 3 contains a graph which shows the linear relationship between Sr ions in a solution and Sr ions in the titanium oxide layer present on the sample.

The ICP-OES analysis was performed first of all on samples treated with the electrolytic solutions as described in Table 1, in the absence of gallium ions and containing strontium ions in different concentrations (0.05M—solution a, 0.08M—solution b, 0.12M—solution c, and 0.15M—solution d), in order to quantify the strontium present in the titanium oxide layer and identify any relationship between the amount of salt in the solution and of ions present on the sample. As shown in the graph in FIG. 3, there is good linearity in the interval of concentrations used; it is therefore possible to predict the amount of strontium deposition on the sample, based on the amount thereof in the solution.

A solution containing the gallium salt and the chelating agent was subsequently added to each of these solutions and it was then verified by means of further ICP-OES analyses that the amount of strontium ions deposited did not vary and the amount of gallium ions deposited was also verified.

At first, two solutions were prepared, with strontium molarities as described above and two different gallium molarities: 0.002M and 0.004M. The ICP-OES analysis showed that the amount of gallium deposited, irrespective of the molarity of the solution, was within a range of values comprised from 5.7 to 19 μg/cm$^2$. Consequently, the solutions containing gallium were considered to be comparable in terms of the treatment obtained.

Example 3—Morphological Characterisation

Different morphological analyses were performed in order to characterise the structure of the oxides deposited on the surface of the titanium alloy Ti$_6$Al$_7$Nb.

The morphological characterisation was carried out in order to evaluate the surface morphology imparted to the samples by the ASD treatment and compare it with that of an untreated sample, i.e. one subjected solely to a surface finishing by sandblasting.

The characterisation was carried out by means of scanning electron microscopy (SEM). The samples analysed were the following:

an untreated sample (NT) subjected solely to a surface finishing by sandblasting, and not to the ASD treatment;

a sample subjected to surface sandblasting and the ASD treatment with an electrolytic solution as described in Table 1, in the absence of strontium ions and with a Ga ion concentration of 0.004 M (Ga);

a sample subjected to surface sandblasting and the ASO treatment with an electrolytic solution as described in Table 1 containing gallium and strontium ions, the latter present at a concentration of 0.08 M. whereas the gallium ions were present at a concentration of 0.002 M (SrGa).

3.1 Analysis with a Scanning Electron Microscope (SEM)

The SEM analyses were performed with two different scanning electron microscopes: SEM Cambridge—Stereoscan 360 and SEM EVO50, the latter also provided with an energy dispersive X-ray spectrometer (EDS probe).

Figure 4:
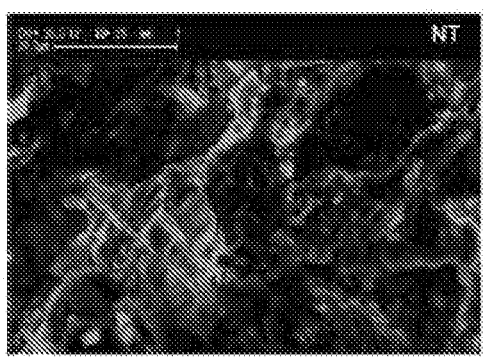
FIG. 4 shows SEM images of an NT sample, an SrGa sample and a Ga sample with 1500× magnification, as described in Example 3.
Figure 4:
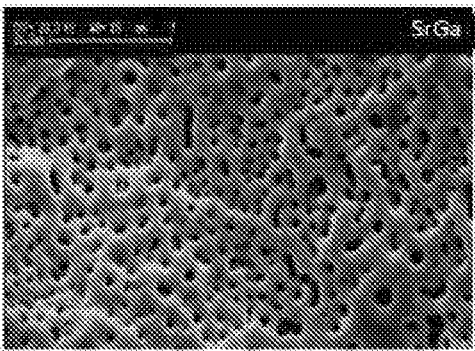
Figure 4:
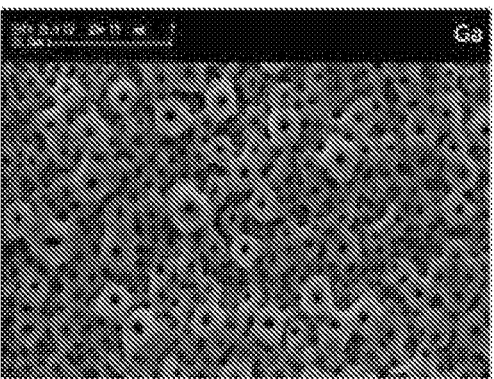

The three samples are shown by way of comparison in FIG. 4. As may be observed, the NT sample has a homogeneously "rough" surface due to the surface finishing process by sandblasting. However, as regards the SrGa and Ga samples, both exhibit a surface porosity having a morphology characteristic of the "spark phenomenon", with a homogeneous pore distribution and little presence of cracks in the oxide. The morphology and size of the pores shows to be slightly irregular, a phenomenon probably tied to the surface finishing pre-treatment performed on the samples.

Figure 5:
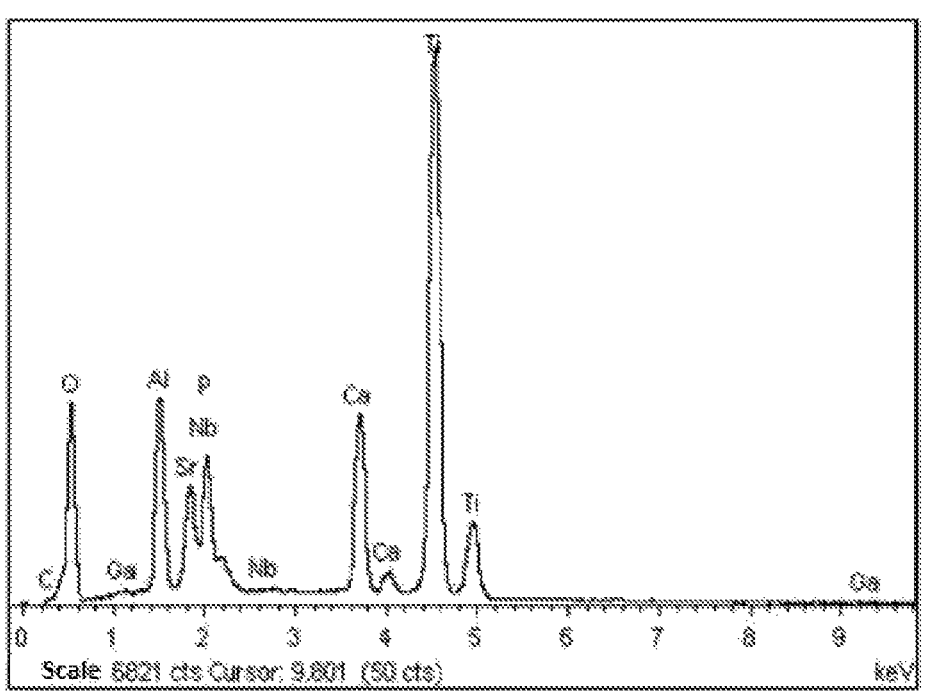
FIG. 5 shows the EDS spectrum of the SrGa sample as described in Example 3.

By using the EDS probe present in the SEM, it was further possible to obtain the spectrum of the SrGa sample shown in FIG. 5. From this spectrum it is possible to see the presence of alloy elements, such as titanium, aluminium and niobium, and also of elements deposited within the oxide by means of the ASD treatment, namely, gallium and strontium, as well, however, as calcium and phosphorus.

3.2 Evaluation of Pore Size

Figure 6:
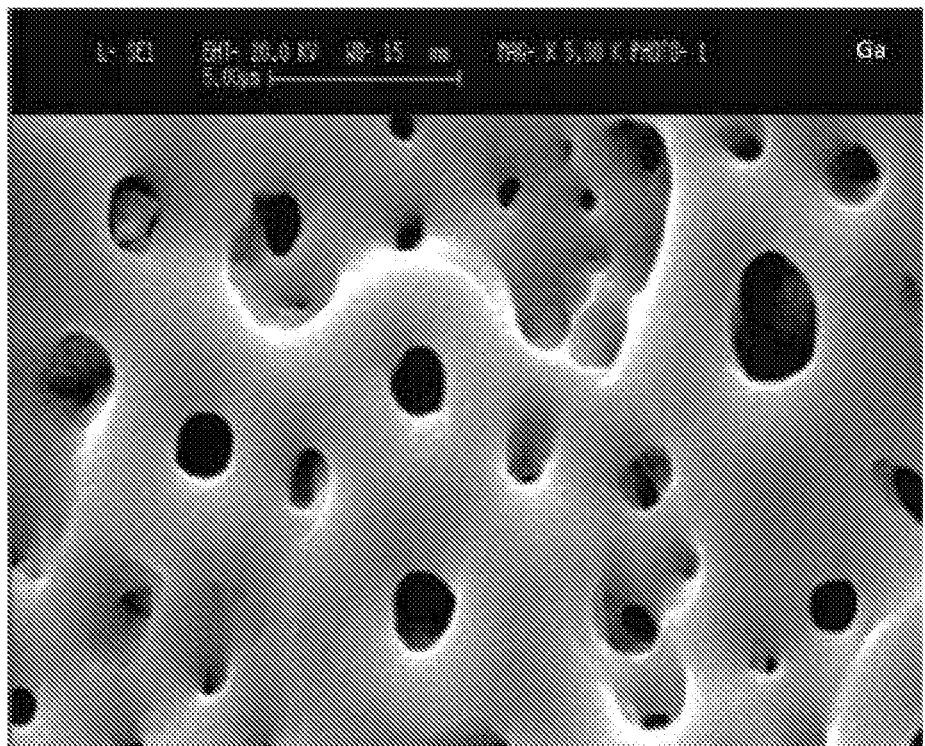
FIG. 6 shows an SEM image of a Ga sample with 5000× magnification, as described in Example 3.

It was possible to measure the diameter of the pores obtained thanks to the acquisition of SEM images of the titanium oxide layer; as noted above. In FIG. 6 it is possible to observe the surface morphology of a Ga sample at a 5000× magnification.

Nine measurements were performed on different pores, whose average size was 1.066 µm.

As regards the SrGa sample, in this case as well the size analysis of the pores the morphologies of the two samples being comparable—provided results consistent with the value given above.

3.3 Evaluation of Oxide Thickness

The thickness of the titanium oxide present on the surface of the samples was evaluated by means of standard metallographic techniques, viewed under an optical microscope and measured by means of Leica LAS—Camera Leica DFC 290 software. For this analysis, two SrGa samples as described previously were prepared and two metallographic cross sections were prepared from them by sectioning the samples using a diamond-coated copper blade. The samples thus cut were subsequently embedded in a heat-curing epoxy resin by means of a hot press (160° C.). In order to obtain smooth, homogeneous surfaces, the samples were polished using abrasive papers with a different particle size, from 120-150 grit to 1500-2000 grit. A final lapping was also performed using an adjustable speed rotating-disc lapping machine with an initial particle size of 5-6 µm and a final one of 0.20-0.10 µm. Following this treatment the surface of the samples showed to be completely smooth. Finally, the samples were rinsed to remove the excess resin and dried; they were then polished with alumina paste (0.3 µm alumina powder).

Figure 7:
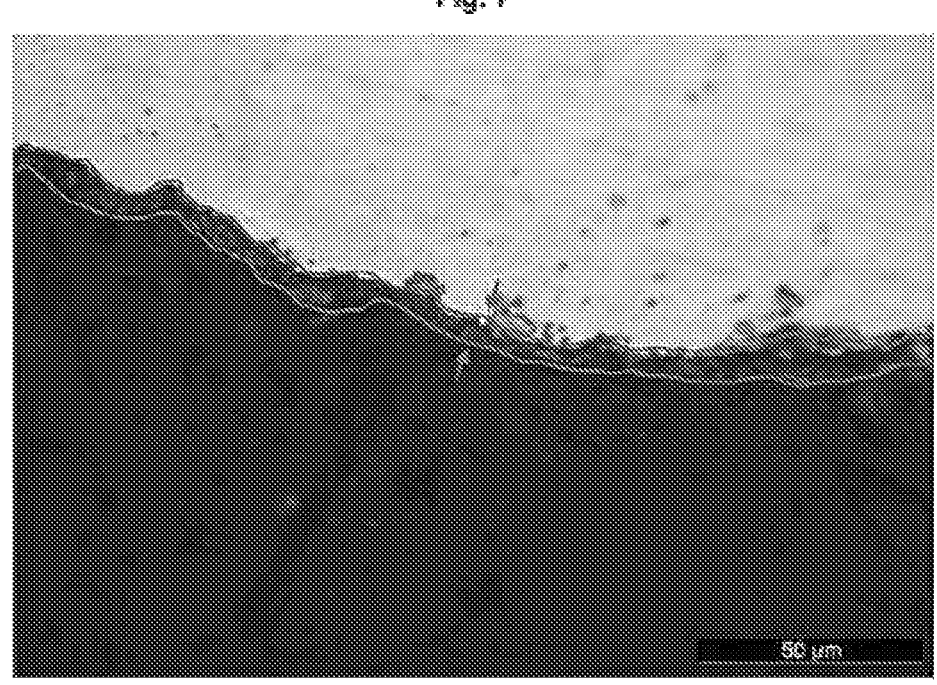
FIG. 7 shows an optical microscope image of the section of an SrGa sample as described in Example 3. The arrows and lines indicate the titanium oxide layer.

Five measurements were performed with an optical microscope for each sample and the mean was then calculated; it turned out to be 7.59±2.56 µm. FIG. 7 shows the optical microscope image of the section of one of the two samples of SrGa where it is possible to appreciate the titanium oxide layer.

Example 4—Physical Characterisation

Physical analyses were carried out with the aim of characterising the titanium oxide layer of the samples treated with ASD from a structural and physical viewpoint.

The samples analysed are the following:

an untreated sample (NT) subjected solely to a surface finishing treatment by sandblasting, and not the ASD treatment;

a sample subjected to surface sandblasting and the ASD treatment with an electrolytic solution as described in Table 1, in the absence of strontium ions and with a Ga ion concentration of 0.004 M (Ga);

a sample subjected to surface sandblasting and the ASD treatment with an electrolytic solution as described in Table 1 containing gallium and strontium ions, the latter present at a concentration of 0.08 M, whereas the gallium ions were present at a concentration of 0.002 M (SrGa).

4.1 Evaluation of the Contact Angle

Wettability is a parameter that conditions the body's biological response to an implanted device.

In order to quantitatively evaluate the wettability of the samples, which depends on the degree of hydrophobicity or hydrophilicity of the surfaces, a measurement was made of the contact angle between the liquid and surface which, in turn, is tied to the surface tension that is established between the liquid molecules.

The contact angle was measured using the sessile drop technique. This technique requires the use of an instrument provided with a syringe dispenser for depositing drops of Millipore water, which expand on the surface of the sample positioned on a movable rest surface. The expansion of the drops continues until an equilibrium is reached between the cohesive forces within the liquid and the gravitational adhesive forces that tend to make the drop spread.

A video system (Allied Vision technologies) consisting of a high-resolution camera connected to a computer captures the images and projects them onto the screen, whilst the Shape Analysis (DSA) (Kruss, Germany) software imposes the baseline for determining the interface between liquid and solid, generates an automatic profile of the drop and provides measurements of the mean contact angle between the values of the two angles identified by the intersection between the profile and baseline.

In order to make the analyses more repeatable and standardised it was necessary to define a protocol that was applied to every sample subjected to analysis. All of the samples were washed with Millipore water on a stir plate for 5 minutes, dried for 15 minutes in an oven at a temperature of 37° C. and allowed to cool to room temperature (25° C.) in a closed container. The samples analysed are two NT samples and two SrGa samples as described in paragraph 4.

Four drops of Millipore water were deposited on every sample and analysed in sequence. The value of the contact angle obtained is the result of the arithmetic mean of the values obtained for every test. The mean values of the angle θ for the NT sample and for the SrGa sample were 81.14°±8.85° and 76.48°±5.15°, respectively.

Figure 8:
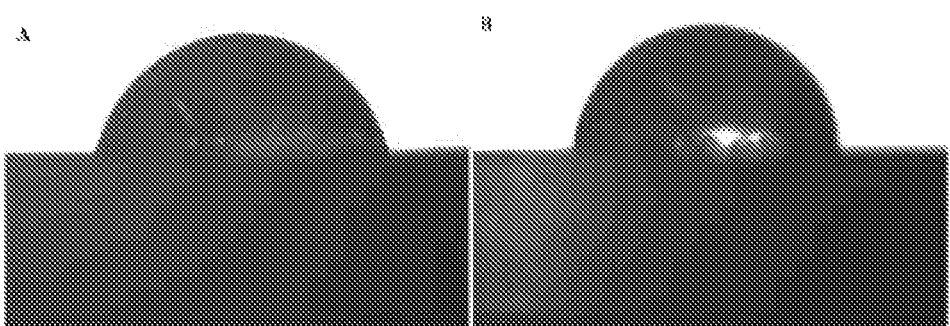
FIG. 8 shows images of a drop of water deposited on the titanium oxide layer coating the surface of an untreated sample (a) and of an SrGa sample (b), as per Example 4.

From FIG. 8 it is moreover possible to qualitatively appreciate the behaviour of the samples in terms of wettability. One observes, in fact, similar drop morphologies of an NT sample and an SrGa sample, confirming the measurements of the contact angles, which show comparable values (p>0.05).

Example 5—Release Tests

In order to examine the release of strontium and gallium ions from the titanium oxide layer, each sample prepared was inserted into a 15 ml conical bottom tube and immersed in 10 ml of phosphate saline buffer solution (D-PSB) (Sigma Aldrich D8537) at 37° C. The release tests were performed also to assess the dissolution, if any, of part of the titanium oxide coating the surface of the samples, with a consequent release of ions incorporated therein.

The samples analysed were SrGa samples, that is, samples subjected to surface sandblasting and an ASD treatment with an electrolytic solution, as described in Table 1, containing gallium and strontium ions, the latter present at a concentration of 0.08 M, whereas the gallium ions were present at a concentration of 0.002 M (SrGa).

The tests were conducted by immersing 12 of these SrGa samples in PBS solution. Four time points were considered: 1 day, 7 days, 14 days and 21 days. Three SrGa samples were prepared for every time point. The test started at the same time for all the samples considered and was interrupted at the previously described time points. At this point ten ml of solution were drawn from two tubes, the third being maintained as a control, and analysed by ICP-OES.

On the twenty-first day the ICP-OES analysis regarded both the solution present in the tube and the samples themselves.

Table 2 shows the mean amounts of strontium and gallium released in PBS at three of the four time points, in terms of mg/l.

TABLE 2

| time point | Sr [mg/l] | Ga [mg/l] |
|---|---|---|
| Day 1 | 0.62 ± 0.17 | 0.05 ± 0.005 |
| Day 7 | 0.57 ± 0.12 | 0.03 ± 0.007 |
| Day 14 | 0.67 ± 0.03 | 0.03 ± 0.003 |

Example 6—Microbiological Characterisation

In order to assess the effectiveness of the antibacterial treatment on the samples treated with ASD, the following microbiological analyses were performed, using the two main bacterial strains involved in orthopaedic infections: *Staphylococcus epidermidis* and *Staphylococcus aureus*, both belonging to the category of gram-positive multidrug-resistant (MDR) strains. The bacterial viability of both strains used for the microbiological tests was evaluated by means of an XTT assay. The results obtained in terms of optical density (O.D.) were normalised with respect to the values detected for the untreated sample (NT) at every time point of the test (day 1, day 3, day 5, day 7).

The samples analysed are the following:

an untreated sample (NT) subjected solely to surface finishing by sandblasting, and not to the ASD treatment;

a sample subjected to surface sandblasting and the ASD treatment with an electrolytic solution as described in Table 1, in the absence of both strontium ions and gallium ions, i.e. in the presence solely of P and Ca ions (matrix);

a sample subjected to surface sandblasting and the ASO treatment with an electrolytic solution as described in Table 1, in the absence of strontium ions and with a Ga ion concentration equal to 0.004 M (Ga);

a sample subjected to surface sandblasting and the ASD treatment with an electrolytic solution as described in Table 1, in the absence of gallium ions and with an Sr ion concentration equal to 0.08 M (Sr);

a sample subjected to surface sandblasting and the ASD treatment with an electrolytic solution as described in Table 1, containing gallium and strontium ions, the latter present at a concentration of 0.08 M, whereas the gallium ions were present at a concentration of 0.002 M (SrGa).

6.1 Prokaryotic Cell Culture Conditions

The strain *Staphylococcus epidermidis* was obtained from a clinical isolate and supplied by the bacteriology and virology unit of the "Azienda Ospedaliero-Universitaria Maggiore della Carità" (Novara, Italy), whilst the strain *Staphylococcus aureus* (ATCC 43300, distributed by LGC Standards, Sesta San Giovanni, Milan, Italy) is commercially available. Both strains were used to assess bacterial adhesion to the samples of titanium alloy according to the present invention. The bacteria were cultured in mannitol agar medium (M9052, Sigma Aldrich) at 37° C. under aerobic conditions for 48 h until the appearance of individual colonies. The plates were kept at 4° C. until the time of use. Before every experiment, 20 ml of fresh bacterial culture were prepared by inoculating about 2-3 individual colonies into Luria Bertani liquid medium solution (LB, Sigma-Aldrich, Milan, Italy). These colonies were cultured at 37° C. in an orbital shaker incubator at 120 rpm for 90 minutes in order to prevent the formation of bacterial precipitates. In order to infect the sample with bacteria in the exponential growth phase, the bacterial suspensions were diluted in PBS so as to reach a final concentration of $1\times10^5$ cells/ml. This concentration was determined by comparing the optical density of the suspensions at 600 nm with a standard curve which correlates optical density ($\lambda$=600 nm) with the number of cells. The value of the final bacterial concentration was determined on the basis of the content of bacteria present in a severe orthopaedic implant infection (about $1\times10^3$ cells/ml), such as to require removal of the prosthesis. During the test, the aim was to simulate the worst case of infection: it was estimated that the maximum level of infection present in an operating room is about $1\times10^3$ cells/ml, so the actual antimicrobial effectiveness of the samples of the present invention was verified by subjecting the sample to even more severe conditions of infection (final bacterial concentration equal to $1\times10^5$ cells/ml).

6.2 Sterilisation of the Samples

The samples were sterilised by immersion in 1 ml of ethanol (Sigm-Aldrich Milan Code R3154) at 70% (v/v) in PBS for two hours and subsequently rinsed in PBS (1 ml each); they were then placed in a 12-well culture plate (Thermo Scientific™ Nunc™, code 142485).

6.3 Infection of the Samples and Biofilm Formation

In order to infect the samples, one millilitre of bacterial solution containing $1\times10^5$ bacteria was deposited on the surface. The cells were left in an incubator for 90 minutes at 37° C., under shaking at 120 rpm, to allow uniform adhesion (adhesion step). The suspension containing the planktonic cells was subsequently removed, whereas the samples with the bacteria adhering to the surface were submerged in 1 ml of LB medium and incubated for 24 hours at 37° C. in a moist atmosphere. The biofilm was allowed to grow at 37° C. for 1,3,5,7 days prior to the evaluation.

The procedure described was followed for both of the bacterial strains on six SrGa samples for every treatment and six untreated samples (NT).

6.4—Evaluation of the Antibacterial Activity of the Alloy Ti₆Al₇Nb

The antibacterial activity was evaluated 1, 3, 5 and 7 days after the bacterial infection by means of an XTT assay, comparing the samples treated with ASO (matrix, Sr, Ga and SrGa) to the untreated ones (NT) used as a control.

6.4.1 XTT Assay

The XTT assay (2,3-Bis-(2-Methoxy-4-Nitro-5-Sulfophe-nyl)-2H-Tetrazoliym-5-Carboxanilide) is a colorimetric assay used to assess cell viability. The XTT salt (Sigma, St Louis, MO USA) was used to determine the activity of the enzyme dehydrogenase as an indicator of the metabolic state of the viable bacterial cells, which convert the XTT yellow tetrazolium salt into a water-soluble brown formazan salt, thus imparting an orange colour to the substance.

The XTT salt was dissolved in acetone (3 mg/ml) and the solution was then diluted to 10% (v/v) with PBS. At every time of evaluation, 100 µl of this solution were deposited on each sample present in the wells of the multiwell plate. The samples were then left to incubate at 37° C. in the dark for 5 hours. Subsequently, 100 µl from every well were centri-fuged for 2 minutes a 1200 rpm and then removed and introduced into a new 96-well plate. The optical density (O.D.) thereof was measured by means of a spectrophotom-eter (Victor, Packardbell, Lainate, Italy) set at 490 nm.

The XTT assay was performed on 6 preparations for every ASD treatment (matrix, Ga, Sr and SrGa) and 6 untreated samples (NT) for both bacterial strains, *Staphylococcus epidermidis* and *Staphylococcus aureus*.

The values of microbial viability relating to the treatments were normalised with respect to the values of untreated titanium.

Figures 9, 10:
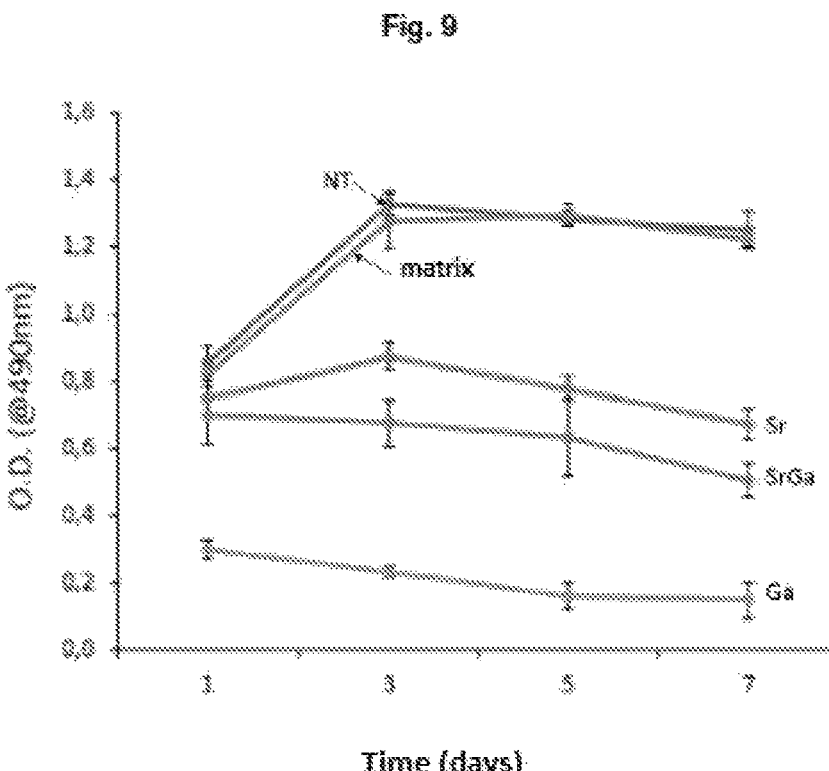
FIG. 9 shows a graph of the cell viability of *S. epidermidis* expressed in terms of optical density (O.D. at 490 nm) on day 1, 3, 5 and 7 in every treatment carried out as per Example 6.
FIG. 10 shows a graph of the cell viability of *S. aureus* expressed in terms of optical density (O.D. at 490 nm) on day 1, 3, 5 and 7 in every treatment carried out as per Example 6.

FIG. 9 and FIG. 10 show the trend in the antibacterial activity of the samples treated with the various solutions at every time point of the test and for both bacterial strains, respectively for *S. epidermidis* and *S. aureus*.

It can be observed that, in the case of *S. epidermidis*, the NT samples show a greater optical density compared to the samples treated with ASD, with the exception of the samples subjected to the ASD treatment with an electrolytic solution in the absence of both strontium ions and gallium ions, i.e. in the presence solely of P and Ca ions ("matrix" samples), whose optical density values are comparable to those of the NT samples. The differences between the Sr and SrGa samples in terms of cell viability are significant (p<0.05) for this strain, except on day 1 and on day 5 (p>0.05).

With regard to *S. aureus*, the NT samples show higher optical density values than the samples treated with ASD, always with significant differences (p<0.05) except for the "matrix" samples on day 3 (p=0.06). The Sr and "matrix" samples subjected to a test with *S. aureus* show similar optical density values, not having any antibacterial (i.e. gallium ions) deposited on them.

As regards the Ga samples, it is possible to observe that in the case of infection both with *S. epidermidis* and with *S. aureus*, very low bacterial viability values are obtained. In the SrGa samples a greater bacterial activity, in terms of optical density, is noted with both bacterial strains compared to the NT samples, thus confirming the presence of the antibacterial, whereas compared to the Ga samples, the antibacterial activity shows to be lower, though in any case acceptable.

This result could be due to the lower amount of gallium ions present on the SrGa sample as opposed to the Ga sample.

Example 7—Biological Characterisation

In vitro tests were performed using two commercial cell lines: human foetal osteoblastic progenitor cells (hFOB 1.19, ATCC CRL-11372) and mature human osteoblasts originating from osteosarcoma (U-2 OS, ATCC HTB-96).

The samples analysed are the following:

an untreated sample (NT) subjected solely to surface finishing by sandblasting, and not to the ASD treat-ment;

a sample subjected to surface sandblasting and the ASD treatment with an electrolytic solution as described in Table 1, in the absence of both strontium ions and gallium ions, that is, in the presence solely of P and Ca ions (matrix);

a sample subjected to surface sandblasting and the ASD treatment with an electrolytic solution as described in Table 1, in the absence of strontium ions and with a Ga ion concentration equal to 0.004 M (Ga);

a sample subjected to surface sandblasting and the ASD treatment with an electrolytic solution as described in Table 1, in the absence of gallium ions and with an Sr ion concentration equal to 0.08 M (Sr);

a sample subjected to surface sandblasting and the ASD treatment with an electrolytic solution as described in Table 1, containing gallium and strontium ions, the latter present at a concentration of 0.08 M, whereas the gallium ions were present at a concentration of 0.002 M (SrGa).

7.1 Sterilisation of the Samples

The samples were initially sterilised by gamma rays, a technique known for its efficiency and ability not to damage titanium alloys.

The samples were subsequently sterilised by immersion with 1 ml of ethanol (Sigma-Aldrich Milan Code R3154) at 70% (v/v) and then washed in PBS. The samples were then placed in a 12-well cell culture plate (Thermo Scientific™ Nunc, code 142485).

7.2 Cell Culture

Culture of U-2 OS Cells

The U-2 OS cells were cultured as per the instructions of the supplier (ATCC) in a commercial medium, fresh Dul-becco's Modified Eagle Medium (DMEM, Sigma-Aldrich Milan) supplemented with antibiotics (penicillin/streptomy-cin, Code P0781, 1% v/v) and foetal bovine serum (FBS, Sigma-Aldrich Milan, Code F7524, 10% v/v) in an incuba-tor at 37° C., 5% $CO_2$.

Culture of the hFOB Cells

The hFOB cells were cultured as per the instructions of the supplier (ATCC) in a commercial medium, fresh Modi-fied Eagle Medium/F12 mix (MEM/F12, Sigma-Aldrich Milan) supplemented with antibiotics (penicillin/streptomy-cin, Code P0781, 1% v/v) and foetal bovine serum (FBS, Sigma-Aldrich Milan, Code F7524, 10% v/v) and selected by means of neomycin (salt G418, Sigma-Aldrich Milan) in an incubator at 34° C., 5% $CO_2$.

7.3 Evaluation of Direct Cytocompatibility

In order to evaluate the cytocompatibility of the treated samples compared to the original titanium alloy, the cells were cultured directly in contact with the treated surface of the samples. Once 70-80% confluence was reached in the plate, the cells (hFOB and U-2 OS) were detached by enzymatic digestion with trypsin (37° C., 5 minutes), centrifuged (5 minutes, 900 rpm) and counted by means of trypan blue staining and a Barker chamber. On the surface of every sample, $1 \times 10^4$ cells were seeded in a volume of 50 microlitres of medium; the cells were allowed to adhere for 2 hours at 37° C., 5% $CO_2$, after which the samples were submerged in 1 ml/sample of fresh medium for direct culturing. The viability of the cells cultured directly on the surfaces of the samples was verified by means of an XTT calorimetric metabolic assay after 1-2-3 days of direct contact as detailed in Example 6 in paragraph 6.4.1.

Figure 11:
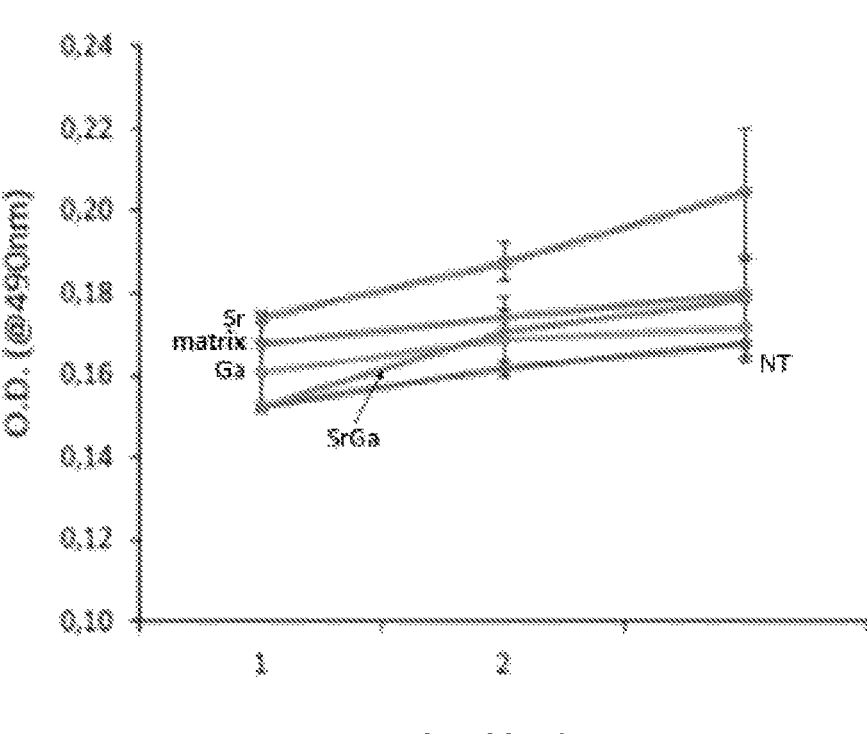
FIG. 11 shows a graph illustrating the trend in cell viability with human foetal osteoblasts (hFOBs) on days 1, 2 and 3 for every treatment carried out as per Example 7.
Figure 12:
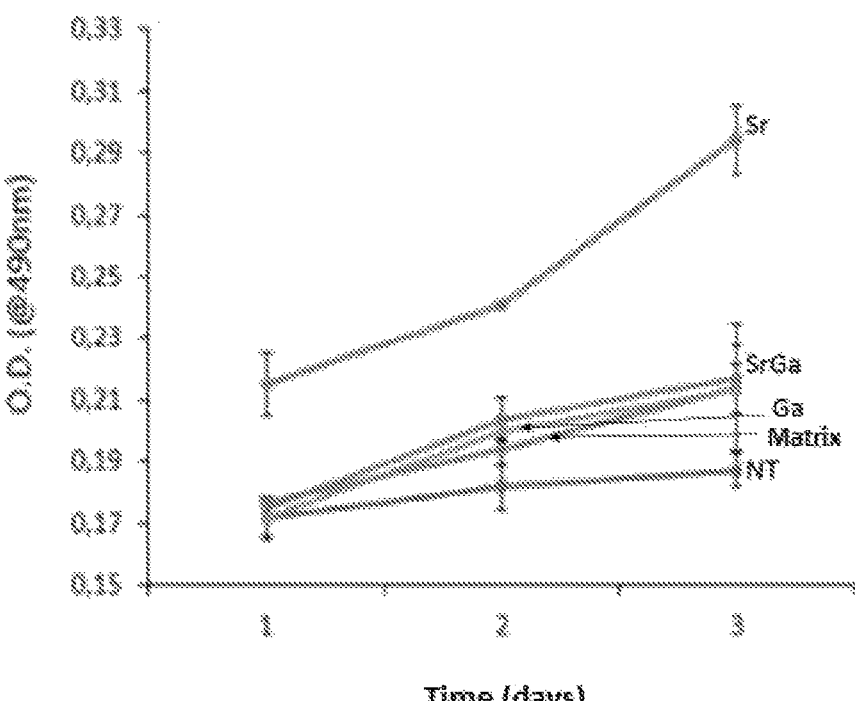
FIG. 12 shows a graph illustrating the trend in cell viability with U-2 OS on days 1, 2 and 3 for every treatment carried out as per Example 7.

The viability values are represented in terms of optical density and normalised with respect to the values of untreated titanium alloy (NT) for every time of evaluation: day 1, day 2 and day 3. In FIG. 11 and FIG. 22 it is possible to see the trend over time, in terms of optical density, of the cell proliferation of both lines, hFOB and U-2 OS, respectively.

For both cell lines it was possible to note a comparable optical density value among the various treatments and the NT samples, with the exception of Sr, which, for the cell line U-2 OS, shows an increase over time in the proliferation of osteoblasts.

This leads one to suppose that strontium may have a positive action on cell proliferation and thus that it actually has an active role in the process of osteointegration. Furthermore, the numerousness of such cells "in vitro" leads one to suppose that, once "in vivo", they may result in a greater deposition of new bone, with consequent benefits in terms of bone stability.

Finally, based on these results, there does not appear to be any cytotoxic effect deriving from the ASD treatments performed on the titanium alloy.

In particular, both on day 2 and on day 3 an increase in the optical density was noted for every sample, thus suggesting an increase in cells on the samples. This increase in optical density was smaller in the case of the NT samples.

These experiments make it possible to conclude that the ASD treatment performed with an electrolytic solution containing gallium shows excellent antibacterial properties but, as it does not include strontium, it does not significantly influence osteointegration, despite not showing any cytotoxic effects. Furthermore, the samples that have a co-deposition of strontium and gallium, though they show slightly less antibacterial activity than the samples with gallium alone, appear to be a good compromise between osteointegrative and antibacterial effectiveness.

The invention claimed is:

1. A prosthesis or a surgical implant comprising a substrate of a metal having at least one surface coated with an oxide layer of the metal itself, wherein said coated surface is modified and enriched with Ca, P, Ga and Sr ions by a morphological and chemical modification of said oxide layer with an anodic spark deposition (ASD) technique; wherein the oxide layer is hydrophilic, and wherein the oxide layer exhibits a combination of antibacterial and osteointegrative actions superior to an oxide layer enriched with Ca, P, and Ga or Ca, P, and Sr.

2. The prosthesis or surgical implant according to claim 1, wherein said coated surface is modified and further enriched with an Ag ion.

3. The prosthesis or surgical implant according to claim 2, wherein said oxide layer of the metal is enriched with an amount of Ag comprised from 0.05 to 5 $\mu g/cm^2$.

4. The prosthesis or surgical implant according to claim 1, wherein said metal is selected from the group consisting of titanium and a titanium alloy.

5. The prosthesis or surgical implant according to claim 1, wherein said oxide layer of the metal has a thickness comprised from 1 to 20 $\mu m$.

6. The prosthesis or surgical implant according to claim 1, wherein said oxide layer of the metal is enriched with an amount of Ga comprised from 0.01 to 30 $\mu g/cm^2$.

7. The prosthesis or surgical implant according to claim 1, wherein said oxide layer of the metal is enriched with an amount of Sr comprised from 10 to 250 $\mu g/cm^2$.

8. The prosthesis or surgical implant according to claim 1, wherein the prosthesis or surgical implant is configured to prevent bacterial colonisation, reduce bacterial biofilm adhesion or promote osteointegration in implantology operations.

9. The prosthesis or surgical implant according to claim 1, wherein said prosthesis or said surgical implant is entirely produced with said substrate.

10. The prosthesis according to claim 1, wherein the oxide layer is a microporous layer having pores of dimensions comprised from 50 nm to 5 $\mu m$.

11. A process for preparing a prosthesis or a surgical implant according to claim 1, comprising the steps of:
- (i) making up an aqueous solution comprising a Ga salt and a chelating agent (solution A) and an aqueous solution comprising an Sr salt, a phosphate, and a calcium salt (solution B);
- (ii) mixing the solution A with the solution B to obtain an electrolytic solution;
- (iii) providing a substrate of a metal, wherein said metal is passivated or non-passivated;
- (iv) optionally pre-treating at least one surface of the substrate of step (iii) until obtaining a surface with a modified morphology;
- (v) providing an electrolytic cell comprising a receptacle (1) containing the electrolytic solution (2) obtained in step (ii), the substrate (3) of step (iii) or the substrate (3) obtained in step (iv), and a cathode and
- (vi) connecting the substrate and the cathode respectively to positive and negative poles of the electrolytic cell and proceeding to treat the substrate by anodic spark deposition (ASD).

12. The process according to claim 11, wherein said step (i) is a step of making up an aqueous solution comprising a Ga salt, a chelating agent, and an Ag salt (solution A'), and wherein said step (ii) is a step of mixing said solution A' with the solution B to obtain an electrolytic solution.

13. The process according to claim 12, wherein the electrolytic solution obtained in step (ii) comprises said Ga salt at a concentration comprised from 0.0001 to 0.002 M.

14. The process according to claim 12, wherein said Ag salt is selected from the group consisting of: silver nitrate ($AgNO_3$) and silver acetate ($AgC_2H_3O_2$).

15. The process according to claim 11, wherein the electrolytic solution obtained in step (ii) comprises said Ga salt at a concentration comprised from 0.001 to 0.008 M.

16. The process according to claim 11, wherein the electrolytic solution obtained in step (ii) comprises said Sr salt at a concentration comprised from 0.01 to 0.3 M.

17. The process according to claim 11, wherein the electrolytic solution obtained in step (ii) comprises said chelating agent at a concentration comprised from 0.002 to 0.01 M, said phosphate at a concentration comprised from 0.02 to 0.2 M, and said calcium salt at a concentration comprised from 0.05 to 0.6 M.

18. The process according to claim 11, wherein the surface with the modified morphology obtained in step (iv) is obtained with a pre-treatment performed by a surface modification technique selected from the group consisting of: sandblasting, coating with metallic titanium by plasma spraying, coating with titanium microspheres sintered onto the surface, coating with titanium fragments, coating with rough or porous titanium, and combinations thereof.

19. The process according to claim 11, wherein said Ga salt is selected from the group consisting of: gallium nitrate $(Ga(NO_3)_3)$, gallium nitrate hydrate $(Ga(NO_3)_3*H_2O)$, and gallium acetate $Ga(C_2H_3O_2)_3$.

20. The process according to claim 11, wherein said Sr salt is selected from the group consisting of: strontium acetate $((CH_3CO_2)_2Sr)$ and strontium nitrate $Sr(NO_3)$ 2.

21. The process according to claim 11, wherein said chelating agent is selected from the group consisting of: L-cysteine $(HSCH_2CH(NH_2)CO_2H)$, oxalic acid, and eth-ylenediaminetetraacetic acid (EDTA).

22. The process according to claim 11, wherein said phosphate is β-glycerophosphate disodium salt pentahy-drate.

23. The process according to claim 11, wherein said calcium salt is calcium acetate monohydrate (CA) $(C_4H_6CaO_4*H_2O)$.

24. The process according to claim 11, wherein said cathode is a metallic cathode; wherein said cathode comprises a titanium cathode.

25. The process according to claim 11, wherein the step of treatment by the anodic spark deposition (step (vi)) is performed at a temperature comprised from −5 to +5° C.

26. The process according to claim 11, wherein the step of treatment by the anodic spark deposition is performed working with direct current at a first current density comprised from 5 to 50 $mA/cm^2$, with a potential that increases independently up to a value comprised from 210 to 330 V, for a period of time necessary to reach said potential value, and at a second current density comprised from 50% to 5% of the value of the first current density or wherein the step of treatment by the anodic spark deposition is performed working with pulsed current.

27. The process according to claim 11, wherein the metal of step (iii) comprises titanium or a titanium alloy.

* * * * *